US006645717B1

(12) United States Patent
Smith et al.

(10) Patent No.: US 6,645,717 B1
(45) Date of Patent: *Nov. 11, 2003

(54) SOLID MEDIUM AND PROCESS FOR THE STORAGE AND RAPID PURIFICATION OF NUCLEIC ACID

(75) Inventors: Martin A. Smith, Brookline, MA (US); Mridula Iyer, Acton, MA (US); Daqing Qu, Newton, MA (US); James C. Davis, Rockland, MA (US)

(73) Assignee: Whatman, Inc., Rockland, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 54 days.

(21) Appl. No.: 09/507,548

(22) Filed: Feb. 18, 2000

Related U.S. Application Data

(62) Division of application No. 09/398,625, filed on Sep. 18, 1999, now abandoned.
(60) Provisional application No. 60/130,716, filed on Apr. 22, 1999, and provisional application No. 60/123,990, filed on Mar. 11, 1999.

(51) Int. Cl.$^7$ .......................... C12Q 1/68; C12P 19/34; G01N 33/00; C07H 21/02; C07H 21/04
(52) U.S. Cl. .................... 435/6; 435/91.1; 435/91.2; 436/94; 536/23.1; 536/24.3; 536/24.33
(58) Field of Search .............. 435/6, 91.1, 91.2, 435/183; 436/94; 536/23.1, 24.3, 24.33, 25.3, 25.4, 25.41

(56) References Cited

U.S. PATENT DOCUMENTS

| 5,496,562 | A |   | 3/1996 | Burgoyne |
| 5,658,548 | A | * | 8/1997 | Padhye et al. ............... 423/335 |
| 5,756,126 | A | * | 5/1998 | Burgoyne .................... 424/488 |
| 5,807,527 | A | * | 9/1998 | Burgoyne .................... 422/488 |
| 5,863,801 | A |   | 1/1999 | Southgate et al. |
| 5,922,591 | A |   | 7/1999 | Anderson et al. |
| 5,939,259 | A |   | 8/1999 | Harvey et al. |

FOREIGN PATENT DOCUMENTS

| WO |       9600348 |   | 6/1996 |
| WO | WO 96/41810   | * | 12/1996 |

OTHER PUBLICATIONS

Lay et al., Real–time fluorescence genotyping of factor V Leiden during rapid–cycle PCR. Clin. Chem. 43, 2262–2267, 1997.*
Van Schie et al., Genomic DNA from saliva using QIAamp Kits. QIAGEN News, issue No. 3, p. 16 and 17, 1998.*
Hints for optimum elution of DNA from QIAprep and QIAquick spin column. QIAGEN News, issue 4, p. 5–7, 1998.*
Isolate DNA from buccal swabs with QIAamp blood kits. QIAGEN News, issue 4, p. 11 and 12, 1998.*
Maatman et al., Purification of bacterial artificial chromosome (BAC) DNA using QIAGEN plasmid kits. QIAGEN News, issue 4, p. 10 and 11, 1996.*
DEPC Water, available since 1995 from Research Genetics, 2130 Memorial Parkway, Huntsville, AL 35801.*
Andersson B, Lu J, Edwards KE, Muzny DM, Gibbs RA., "Method for 96–well M13 DNA template preparations for large–scale sequencing". *Biotechniques.* Jun. 1996;20(6):1022–7.
Baron H, Fung S, Aydin A, Bahring S, Luft FC, Schuster H., "Oligonucleotide ligation assay (OLA) for the diagnosis of familial hypercholesterolemia". *Nat. Biotechnol.* Oct. 1996;14(10):1279–82.
Belgrader P, Del Rio SA, Turner KA, Marino MA, Weaver KR, Williams PE., "Automated DNA purification and amplification from blood–stained cards using robotic workstation". *Biotechniques.* Sep. 1995;19(3): pp. 426–32.
Connolly BA, Rider P., "Chemical Synthesis of oligonucleotides containing a free sulphydryl group and subsequent attachment of thiol specific probes". *Nucleic Acids Res.* Jun. 25, 1985;13(12): pp. 4485–502.
Connolly BA., "The synthesis of oligonucleotides containing a primary amino group at the 5'–terminus". *Nucleic Acids Res.* Apr. 10, 1987;15(7):3131–9.
Ibrahim MS, Lofts RS, Jahrling PB, Henchal EA, Weedn VW, Northrup MA, Belgrader P., "Real–time microchip PCR for detecting single–base differences in viral and human DNA". *Anal Chem.* May 1, 1998;70(9):2013–7.
Belgrader P, Marino MA., "Automated Sample Processing Using Robotics for Genetic Typing of Short Tandem Repeat Ploymorphisms by Capillary Electrophoresis". *Laboratory Robotics and Automation.* (9):pp. 3–7.
Del Rio SA, Marino MA, Belgrader P., "Reusing the same blood–stained punch for sequential DNA amplifications and typing". *Biotechniques.* Jun. 1996;20(6):pp. 970–972, 974.

(List continued on next page.)

*Primary Examiner*—Ethan C. Whisenant
*Assistant Examiner*—Frank Lu
(74) *Attorney, Agent, or Firm*—Edwards & Angell, LLP

(57) ABSTRACT

A medium for storage and subsequent analysis of a genetic material includes a support for immobilizing the genetic material thereon and allowing subsequent elution of the genetic material therefrom and a coating functionally associated with the support for enabling cellular lysis and releasing the genetic material from the lysed cells while stabilizing the immobilized released genetic material.

A method of storing the genetic material and subsequently analyzing the genetic material includes the steps of immobilizing the genetic material on a support while enabling cellular lysis and release of genetic material from the lysed cells and stabilizing the immobilized released genetic material on the support. The genetic material is then eluted to generate a soluble genetic material fraction. The eluted genetic material can be analyzed.

15 Claims, 10 Drawing Sheets

OTHER PUBLICATIONS

Itoh M, Carninci P, Nagaoka S, Sasaki N, Okazaki Y, Ohsumi T, Muramatsu M, Hayashizaki Y., "Simple and rapid preparation of plasmid template by a filtration method using microtiter filter plates". *Nucleic Acids Res.* Mar. 15, 1997;25(6):1315–6.

Khandjian EW, Meric C., "A procedure for Northern blot analysis of native RNA". *Anal Biochem.* Nov. 15, 1986;159(1)pp. 227–32.

Ledray LE, Netzel L., "DNA evidence collection". *J Emerg Nurs.* Apr. 1997;23(2):156–8.

Rogers C, Burgoyne L., "Bacterial typing: storing and processing of stabilized reference bacteria for polymerase chain reaction without preparong DNA—an example of an automobile procdure". *Anal Biochem.* May 1, 1997;247(2):223–7.

Sanger F, Nicklen S, Coulson AR., "DNA sequencing with chain-terminating inhibitors". *Proc. Natl. Acad. Sci USA* Dec. 1977; 74(12):pp. 5463–5467.

Yang Q, Goldstein IJ, Mei HY, Engelke DR., "DNA ligands that bind tightly and selectively to celloboise". *Proc Natl Acad Sci U S A.* May 12, 1998;95(10):5462–7.

Church GM, Gilbert W., "Genomic sequencing". *Proc Natl Acad Sci U S A.* Apr. 1984;81(7):1991–5.

Armstrong J.W., Gerren R.A., Hamilton S.D., "A Review of Automation Options to Support Plate Preparation, Cherry Picking, and Homogeneous Assays". *Journal of Biomolecular Screening.* 1998 (3) 4: pp. 271–275.

Coull, J.M., Weith, H. L., Bischoff, R., "A Novel Method for the Introduction of an Aliphatic Primary Amino Group at the 5' Terminus of Synthetic Oligonucleotides". *Tetrahedron Letters*, 1986; (27) 34:pp. 3991–3994.

*Molecular Cloning: A Laboratory Manual.* Sambrook. Cold Spring Harbor Laboratory Press:1989: pp. 9.1–9.62, 10.51–10.67, 11.31–11.32, 11.40–11.44, 14.1–14.35.

Panteleeff DD, John G, Nduati R, Mbori–Nbacha D, Richardson B, Kreiss J, Overbaugh J., "Rapid method for screening dried blood samples on filter paper for human immunodeficiency virus type 1 DNA". *J Clin Microbiol.* Feb. 1999;37(2):350–3.

Ramanujan R, Anhalt M, Blair P, Burdick B., "Stabilization of nucleic acids in whole blood: an alternative to Guthrie cards". *Biotechniques.* Nov. 1993;15(5):825–7.

Erlich HA., PCR Technology: Principles and Applications for DNA Amplification. 1989. Stockton Press. pp. ix–x, 1–16, 31–60, 149–151.

\* cited by examiner

1 = 0ng/ml
2 = 10ng/ml
3 = 100ng/ml
4 = 500ng/ml
5 = 1000ng/ml

| Filter material | RFU | Calculated Yield |
|---|---|---|
| FTA | 1.073 | 60.2ng |
| Filter Mem. Invention. | 7.751 | 300ng |

| Starting Volume Saliva (ul) | Yield of Genomic DNA (ng) |
|---|---|
| 5 | 141 |
| 10 | 211 |
| 50 | 222 |
| 100 | 356 |

| Step | Roche | Promega | Filter Mem. Invent |
|---|---|---|---|
| Apply Blood | Yes | Yes | Yes |
| 1st Lysis | 10 min | 10 min | Instant (0 min) |
| Centrifuge | 5 min | 2 min | No |
| Wash Buffer | No | No | 3x (15 min) |
| Remove S/N | Yes | Yes | No |
| 2nd Lysis | 65°C 5 min | 56°C 20 min | No |
| Centrifuge | 3 min | No | No |
| Remove S/N | Yes | No | No |
| Vortex | 1 min | 10 seconds | No |
| Elution | No | 100°C 8 min | 100°C 10 min |
| Centrifuge | No | 2 min | 2 min |
| Total time | 24 min | 42 min | 27 min |

FIG. 7A

| Method | RFU | Total Yield (ng) |
|---|---|---|
| Filter Mem. Invention | 4.785 | 180 |
| Roche (Split Second) | 4.901 | 197 |
| Promega (Amp Ready) | 4.537 | 168 |

SOLID MEDIUM AND PROCESS FOR THE STORAGE AND RAPID PURIFICATION OF NUCLEIC ACID

CROSS-REFERENCE TO RELATED APPLICATIONS

This application is a divisional of U.S. patent application Ser. No. 09/398,625, filed Sep. 18, 1999, now abandoned which is incorporated herein by reference, and which is a conversion of U.S. Provisional Patent Application Ser. No. 60/130,716, filed Apr. 22,1999, and this application also claims the benefit of U.S. Provisional Application Ser. No. 60/123,990, filed Mar. 11, 1999.

FIELD OF THE INVENTION

The present invention relates to medium and methods for storage and subsequent purification of nucleic acids or genetic material from whole cells. In particular, the invention relates to the storage and purification of nucleic acids from a biological mixture of molecules in a fluid phase on a support. The purified nucleic acid may then be utilized for a variety of analyses such as amplification by the polymerase chain reaction (PCR) (PCR Technology: Principles and Applications for DNA Amplification, H. Erlich (ed) Stockton Press 1989), genotyping, sequencing (Sanger et al (1977) DNA Sequencing with Chain Terminating Inhibitors P. N. A. S. 74: 5463), optical density quantitation, southern and northern blotting, fluorescent detection, making molecular probes, and cloning (Molecular Cloning, Sambrook et al. (1989)).

DESCRIPTION OF BACKGROUND ART

Genotyping is the discipline of identifying an individual's genome in relation to disease specific alleles and/or mutations that occur as an effect of parental linkage. The rapid purification of human genomic DNA is an essential part of a genotyping process; the genomic DNA of an individual being the structural unit for the entire DNA sequence of every allele expressed.

Human genomic DNA cannot be directly sequenced. In order to carry out sequence analysis on regions of the chromosomes that may contain portions of mutation or disease specific sequences, selected portions are amplified via PCR and the amplified products sequenced. The selected portions of the chromosomes that are amplified are dictated by the specific sequence of the primers used in the PCR amplification. The primer sets that are used in genotyping studies are commercially available and are representative for the chromosome under examination. Therefore, if linkage studies identify that a disease bearing sequence is on a particular chromosome, then many primer sets will be utilized across that chromosome in order to obtain genetic material for sequencing. The resultant PCR products may well represent the entire chromosome under examination. Due to the large length of chromosomes, many PCR reactions are carried out on the genomic DNA template from a single patient.

Human genomic DNA is purified by a variety of methods (Molecular Cloning, Sambrook et al. (1989)). Consequently, many commercial kit manufacturers provide products for such techniques, for example: AmpReady™ (Promega, Madison, Wis.), DNeasy™ (Qiagen, Valencia, Calif.), and Split Second™ (Roche Molecular Biochemicals, Indianapolis, Ind.). These products rely on the use of specialized matrices or buffer systems for the rapid isolation of the genomic DNA molecule.

More recently, microporous filter-based techniques have surfaced as tools for the purification of genomic DNA as well as a whole multitude of nucleic acids. The advantage of filter-based matrices are that they can be fashioned into many formats that include tubes, spin tubes, sheets, and microwell plates. Microporous filter membranes as purification support matrices have other advantages within the art. They provide a compact, easy to manipulate system allowing for the capture of the desired molecule and the removal of unwanted components in a fluid phase at higher throughput and faster processing times than possible with column chromatography. This is due to the fast diffusion rates possible on filter membranes.

Nucleic acid molecules have been captured on filter membranes, generally either through simple adsorption or through a chemical reaction between complementary reactive groups present on the filter membrane or on a filter-bound ligand resulting in the formation of a covalent bond between the ligand and the desired nucleic acid.

Porous filter membrane materials used for non-covalent nucleic acid immobilisation have included materials such as nylon, nitrocellulose, hydrophobic polyvinylidinefluoride (PVDF), and glass microfiber. A number of methods and reagents have also been developed to also allow the direct coupling of nucleic acids onto solid supports, such as oligonucleotides and primers (eg. J. M. Coull et al., Tetrahedron Lett. Vol. 27, page 3991; B. A. Conolly, Nucleic Acids Res., vol. 15, page 3131, 1987; B. A. Conolly and P. Rider, Nucleic Acids Res., vol. 12, page 4485, 1985; Yang et al P.N.A.S. Vol.95: 5462–5467). UV cross-linking of DNA (Church et al., PNAS, vol. 81, page 1991, 1984), The Generation Capture Column Kit (Gentra Systems, Minneapolis, Minn.) and RNA (Khandjian, et al., Anal. Biochem, Vol. 159, pages 227, 1986) to nylon membranes have also been reported.

Many chemical methods have been utilized for the immobilization of molecules such as nucleic acids on filter membranes. For example, activated paper (TransBind.TM, Schleicher & Schuell Ltd., Keene, N.H.) carbodimidazole-activated hydrogel-coated PVDF membrane (Immobilin-IAV.TM, Millipore Corp., Bedford, Mass.), MAP paper (Amersham, Littlechalfont Bucks, Wis.), activated nylon (BioDyne. TM, Pall Corp., (Glen Cove, N.Y.), DVS- and cyanogen bromide-activated nitrocellulose. Membranes bound with specific ligands are also known such as the SAM2TM Biotin Capture Membrane (Promega) which binds biotinylated molecules based on their affinity to streptavidin or MAC affinity membrane system (protein A/G) (Amicon, Bedford, Mass.). Some of the disadvantages of covalent attachment of biomolecules onto activated membranes are:

a) Molecule immobilization is often slow requiring 20–180 minutes for reaction completion.

b) High ligand and biomolecule concentration is needed for fast immobilization.

c) Constant agitation is needed during the immobilization process that may result in biomolecule denaturation and deactivation.

d) Once the immobilization process is complete, often a blocking (capping) step is required to remove residual covalent binding capacity.

e) Covalently bound molecules can not be retrieved from the filter membrane.

There is a need for a nucleic acid immobilization procedure that exhibits the high specificity of covalent immobilization onto the filter membrane without the use of harsh chemical reactions and long incubation times. In particular there is a need for the capture and separation of nucleic acids from a mixture in a fluid phase onto a filter membrane matrix. Of special interest is the ability to store or archive the bound nucleic acids on the filter membrane matrix.

More recently, glass microfiber, which has been shown to specifically bind nucleic acids from a variety of nucleic acid containing sources very effectively (for example see: Itoh et al (1997) Simple and rapid preparation of plasmid template by filtration method using microtiter filter plates. NAR, vol. 25, No. 6: 1315–1316; Andersson, B. et al (1996) Method for 96-well M13 DNA template preparations for large-scale sequencing. BioTechniques vol. 20: 1022–1027). Under the correct salt and buffering conditions, nucleic acids will bind to glass or silica with high specificity.

Based on U.S. Pat. Nos. 5,496,562, 5,756,126, and 5,807,527, it has been demonstrated that nucleic acids or genetic material can be immobilized to a cellulosic-based dry solid support or filter (FTA filter). The solid support described is conditioned with a chemical composition that is capable of carrying out several functions: (i) lyse intact cellular material upon contact, releasing genetic material, (ii) enable and allow for the conditions that facilitate genetic material immobilization to the solid support (probably by a combination of mechanical and chaotrophic), (iii) maintain the immobilized genetic material in a stable state without damage due to degradation, endonuclease activity, UV interference, and microbial attack, and (iv) maintain the genetic material as a support-bound molecule that is not removed from the solid support during any down stream processing (as demonstrated by Del Rio et al (1995) BioTechniques. Vol. 20: 970–974).

The usefulness of the so called FTA cellulosic filter material described in U.S. Pat. Nos. 5,496,562, 5,756,126, and 5,807,527 has been illustrated for several nucleic acid techniques such as bacterial ribotyping (Rogers, C & Burgoyne, L (1997) Anal. Biochem. Vol. 247: 223–227), detection of single base differences in viral and human DNA (Ibrahim et al (1998) Anal. Chem. Vol. 70: 2013–2017), DNA databasing (Ledray et al (1997) J. Emergency Nursing. Vol.23, No. 2: 156–158), automated processing for STR electrophoresis (Belgrader, B & Marino, M (1996) L.R.A. vol.9: 3–7, Beigrader et al (1995) BioTechniques. Vol. 19, No. 3: 427432), and oligonucleotide ligation assay for diagnostics (Baron et al (1996) Nature Biotech. Vol 14:1279–1282).

It has been shown that nucleic acid or genetic material applied to, and immobilized to, FTA filters cannot be simply removed, or eluted from the solid support once bound (Del Rio et al (1995) BioTechniques. Vol. 20: 970–974). This is a major disadvantage for applications where several downstream processes are required from the same sample, such a STR profiling and genotyping.

Currently, cellular material is applied to FTA filter media, and generally the cellular material, once applied forms a spot on the FTA filter. From this spot, small punches can be taken; each small punch will have immobilized to it enough nucleic acid or genetic material to facilitate a single downstream process such as a PCR reaction. As the two primers administered to a PCR reaction are presented in solution, it is of no consequence that the cellular nucleic acid template is immobilized to the filter. All amplicon will be formed in solution. Amplicon can then be readily removed from the reaction by aspirating the liquid phase away from the FTA solid filter punch. Therefore, for multiple processing from a single sample, many punches have to be taken. Multiple punching is very time consuming, and as yet, has not lent itself to simplified automation.

It is much more desirable to provide nucleic acid as a soluble fraction from which aliquots can be readily dispensed to as many reactions as required. Automated liquid handling of this type is a fundamental technique within the pharmaceutical and other industries (for example see: Armstrong et al (1998) J. Biomolecular Screening. Vol. 3, No. 4: 271–275).

SUMMARY OF THE INVENTION

In accordance with the pr esent invention, there is pr ovided a medium for storage and subsequent analysis of a genetic material, the medium including a support for immobilizing a genetic material thereon and for allowing subsequent elution of genetic material therefrom. A coating is functionally associated with the support for enabling cellular lysis and releasing the genetic material from the lysed cells while stabilizing the immobilized released genetic material. A method for storing the genetic material and subsequently analyzing the genetic material includes the steps of immobilizing the genetic material on the support while enabling cellular lysis and release of genetic material from the lysed cells. The immobilized released genetic material is stabilized. The genetic material is then eluted to generate a soluble genetic materi al fraction. The eluted genetic material is subsequently analyzed.

BRIEF DESCRIPTION OF THE DRAWINGS

FIG. 7 is a table of protocol steps and total time required for genomic DNA prepared from blood using commercially available kits compared to the filter membrane of the invention;

FIG. 7b is a table of the yields of genomic DNA prepared from blood using commercially available kits compared to the filter membrane of the invention;

DETAILED DESCRIPTION OF THE INVENTION

The present invention most generally provides a medium for storage and subsequent analysis of the genetic material, the medium generally including a support for immobilizing a genetic material thereon and allowing subsequent elution of the genetic material therefrom. A coating is functionally associated with the support for enabling cellular lysis and releasing the genetic material from the lysed cells while stabilizing the immobilized released genetic material. A method is also provided of storing a genetic material most generally including the steps of immobilizing a genetic material on the support which allows subsequent elution of the genetic material and lysing cells and releasing the genetic material from the lysed cells while stabilizing the immobilized released genetic material. The genetic material can then be analyzed in solution as opposed to being immobilized on the support.

The chemical composition of the support facilitates the lysis of whole cells and the subsequent capture of the released nucleic acids. The chemical composition further aids in their long term storage. The composition of the support is such that the rapid purification of the captured nucleic acid can be carried out. That is, the support itself allows for the release of nucleic acid by an elution step thereby providing a soluble nucleic acid fraction. As discussed in more detail below and exemplified in the following examples, the present invention is most efficient with regard to elution of total DNA from the sample.

Preferably, the support of the present invention is a porous material in the form of a filter membrane as described and defined below.

Unexpectedly, it has now been discovered that a support, when processed in accordance with the invention, to provide a nucleic acid eluting filter material provides a number of advantages and applications as described hereinafter over the prior art discussed above. Thus, use of the media of the present invention now provides advantages of faster processing of nucleic acid-containing biological fluids as well as multiple processing of fluids.

Figure 9:
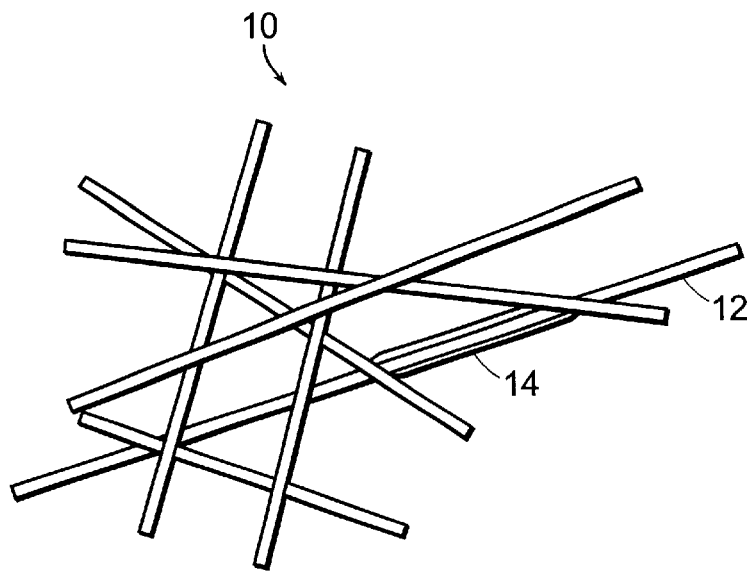
FIG. 9 is a cross-sectional view of a filter membrane made in accordance with the present invention.

The present invention, generally shown at 10 in FIG. 9, includes the following components:

(i) a suitable support, preferably a filter membrane 12; and (ii) a chemical coating 14.

Reaction of the filter membrane with the chemical coating solution produces the filter membrane of the invention. If the membrane is fibrous, this coating is a coating of the filter fibers, not the filter surface.

The term "filter membrane" as used herein means a porous material or filter media formed, but not limited to, either fully or partly from glass, silica or quartz including their fibers or derivatives thereof. Other materials from which the filter membrane can be composed also include cellulose-based (nitrocellulose or carboxymethylcellulose papers), hydrophilic polymers including synthetic hydrophilic polymers (eg. polyester, polyamide, carbohydrate polymers), polytetrafluoroethylene, and porous ceramics.

The media used for the filter membrane of the invention includes any material that does not inhibit the sorption of the chemical coating solution and which does not inhibit the storage, elution and subsequent analysis of nucleic acid-containing material added to it. This includes flat dry matrices or a matrix combined with a binder. It is preferred that the filter membrane of the invention be of a porous nature to facilitate immobilization of nucleic acid. Unlike prior art supports, the support of the present invention allows for elution of the genetic material therefrom in a state that allows for subsequent analysis. Unexpectedly, such elution is a time efficient step thereby providing for almost immediate analysis.

The term "chemical coating solution" as used herein means a chemical composition that is able to sorb to the aforementioned filter membrane. The composition of the chemical coating solution is as described and relates to that outlined in U.S. Pat. Nos. 5,756,126, 5,807,527, and 5,496,562. Adsorption of the chemical coating solution to the selected filter membrane results in the formation of the filter membrane of the invention.

More specifically, the chemical coating solution includes a protein denaturing agent and a free radical trap. The denaturing reagent can be a surfactant that will denature proteins and the majority of any pathogenic organisms in the sample. Anionic detergents are examples of such denaturing reagents. The chemical solution can include a weak base, a chelating agent, and the anionic surfactant or detergent, and optionally uric acid and urate salt as discussed in detail in the above-cited U.S. Pat. No. 5,807,527. More preferably, the weak base can be a Tris, trishydroxymethyl methane, either as a free base or as the carbonate, and the chelating agent can be EDTA, and the anionic detergent can be sodium dodecyl sulfate. Other coatings having similar function can also be utilized in accordance with the present invention.

The term "functionally associated with" means that the coating is disposed, sorbed, or otherwise associated with the support of the present invention such that the support and coating function together to immobilize nucleic acid thereon through an action of cellular lysis of cells presented to the support. That is, the coating can be adsorbed, absorbed, coated over, or otherwise disposed in functional relationship with the media. For example, the support, in the form of a filter membrane, can be disposed in a solution containing the chemical solution. As stated above, the support of the present invention is preferably a porous filter media and can be in the form of a flat, dry media. The media can be combined with a binder, examples of binders well-known in the art being polyvinylacrylamide, polyvinylacrylate, polyvinylalcohol, gelatin, for example.

It is critical that the support of the present invention be capable of releasing the genetic material immobilized thereto by a heat elution. Preferably, such a heat elution is accomplished by the exposure of the support having the genetic material stored thereon to heated water, the water being nuclease free. This capacity to allow for elution characterizes the various support materials of the present invention.

The term "filter membrane of the invention" as used herein means functional solid supports or matrices that enables the specific immobilization of nucleic acid, through an action of cellular lysis. Nucleic acid may be presented to it in the form of nucleic acid-containing material such as blood, cultured mammalian cells, saliva, urine, cultured bacterial cells, yeast, solid tissue, faeces, lymphatic fluid, amniotic fluid, plant tissue, and the like. The filter membrane of the invention is such that nucleic acid immobilized to it can remain so in a stable form, not exhibit degradation, shearing, endonuclease digestion, nor UV damage.

The filter membrane of the invention is such that at any point during a storage regime, it allows for the rapid purification of immobilized nucleic acid. The invention is such that immobilized nucleic acid is collected in the form of a soluble fraction following a simplified elution process, during which immobilized nucleic acid is released from the filter membrane of the invention. The filter membrane of the invention yields nucleic acid of sufficient quality that it does not impair downstream analyses such as polymerase chain reaction (PCR), ligase chain reaction (LCR), transcription mediated amplification (TMA), reverse transcriptase initiated PCR, DNA or RNA hybridization techniques, sequencing, and the like.

Nucleic acid immobilized to a solid filter support, although a suitable template for singular PCR reactions, cannot be measured or detected by traditional techniques such as optical density or fluorescence. Nucleic acid has to be in solution for these techniques. Other post purification techniques where nucleic acid is desired in the soluble form includes: cloning, hybridization protection assay, bacterial transformation, mammalian transfection, transcription-mediated amplification, and the like. The present invention provides nucleic acid in such a soluble form.

The filter membrane of the invention can possess the same chemical component as FTA that enables the action of cellular lysis and nucleic acid release upon sample application. The chemical component ensures nucleic acid stability via protein denaturants, a free radical trap, and viral/microbial inhibitors. The difference between prior art FTA solid supports and the filter membrane of the invention is that the base solid support, or filter, has been changed compared to that described for FTA products. This change in solid support material, or filter, has enabled, upon a simplified heat elution step, bound nucleic acid to be removed from the filter membrane of the invention whereas it cannot be removed from FTA solid support (see Del Rio et al (1995) BioTechniques. Vol. 20: 970–974). The nucleic acid released from the filter membrane of the invention is thus presented as a soluble fraction that can be readily aliquoted to multiple downstream processes such as PCR amplification. The eluted soluble nucleic acid can also be entered into techniques where soluble nucleic acid is a necessity such as optical density analysis, fluorescence detection, cloning, transformation, and the like. This added technique of elution enables high throughput multiple processing regimes, such as genotyping.

Figure 10:
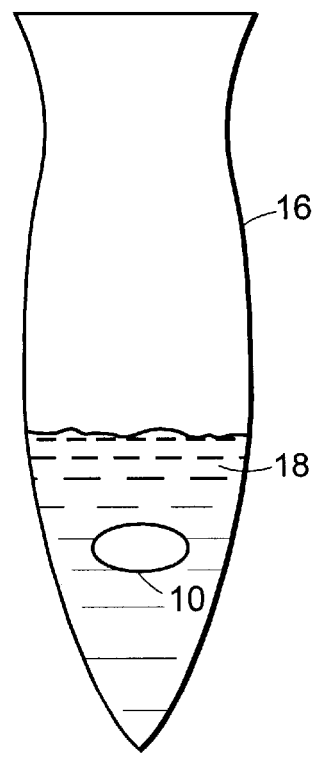
FIG. 10 is a cross-section of a device made in accordance with the present invention.

As discussed below in the experimental section, it can be advantageous to provide a device for storage and subsequent analysis of genetic material wherein a sample can be collected, such as a fluid sample in the form of blood or saliva. As shown in FIG. 10, the device can include a container, such as a tube 16, containing the media 10 constructed in accordance with the present invention. The container must be non-reactive with the genetic material. Examples of such containers can be a tube 16 made from a polymer selected from the group consisting of common polypropylene, but also polysulphone. As shown in FIG. 10, a sample 18 has been disposed within the tube 16 thereby exposing the media disk, in a free floating form within the tube 16, to the sample. As discussed below in greater detail in the experimental section, the method of the present invention can be utilized to immobilize genetic material from the sample onto the media 10.

The present invention further provides, most generally, a method for storing the genetic material and subsequently analyzing genetic material by the steps of immobilizing the genetic material on the support while enabling cellular lysis and release of the genetic material from the lysed cells. The chemical coating on the support, in the form of the filter media, enables the lysing of the genetic material and stabilization of the immobilized released genetic material. The support allows for eluting of the genetic material to generate the soluble genetic material fraction, thereby allowing for subsequent analysis of the genetic material, as discussed above.

The eluting step can be accomplished by heating the support having the genetic sample immobilized thereon, the support releasing the heated genetic material therefrom and into solution, preferably into a nuclease free water. Most preferably, this is accomplished by disposing the support having the genetic immobilized thereon into heated water, the water being heated preferably between 65° C. and 100° C.

As discussed in greater detail in the examples below, various washes can be performed in various types of buffers. Preferably, the washing buffers can be selected from the group including Tris/EDTA; 70% ethanol; STET; SSC; SSPE FTA purification reagent, and the like.

The present invention can find utility in many areas of genomics. For example, the present invention provides the capability to elute bound genetic material for the rapid purification of the genetic material to be utilized in any number of forensic applications, such as identification, patemity/maternity identification, and at the scene of a crime.

Prisoners from many countries are required to give a genetic sample (blood or buccal sample) for DNA fingerprinting purposes. The use of the present invention provides a means for the long term storage of prisoner genetic material. If necessary, the genetic material can be tested as soon as it is taken or many years after storage. The genetic material can be obtained as either a soluble or solid phase fraction once isolated on the filter media of the present invention.

The present invention can be utilized for patemity/matemity identification having a particular use for a mother or hospital wherein a newborn has been mislaid in the hospital. The rapid ability of the present invention to provide for a purified genetic sample provides even greater utility in such instances where a speedy identification of a mislaid child would be most propitious.

The present invention is a significant contribution to current methodology for the preparation of soluble genetic material which are otherwise time consuming and often result in inadequate template that is damaged or contaminated. The present invention provides high yield of purified genetic material of superior quality in less than twenty minutes of laboratory time. The rapidly purified genetic material can be utilized for any number of food/agricultural applications such as tracing, breeding, identification, and cloning.

The efficiency with which food manufacturers detect pathogenic outbreak in both their livestock and finished product is the measure of a successful company. The use of the present invention as a swab that can be simply pressed against food or the use of a card onto which carcass blood can be spotted enables uses of the present invention to rapidly isolate and detect for the presence of pathogenic genetic material. Time consuming prior art assay techniques and involved nucleic acid preparations do not need to be performed if the present invention is utilized. Collected pathogenic nucleic acid can be used as a soluble fraction or solid phase fraction with the choice of an elution step.

Tracing carcass material, whether for legal or health issues, enables manufacturers to keep control of their products. At the point of kill in a slaughter house, a card utilizing the present invention can be attached to the carcass onto which its blood has been spotted. At the same time, a second card can be spotted with the same blood and kept as an archive at the slaughter house. If an identification issue arises for a certain carcass, genetic records on both the carcass and the slaughterhouse can be utilized. If the carcass card is inadvertently removed, identification can still be carried out by simply pressing a carcass flesh onto such a card.

Identifying the desired genes and characteristics that are required for a subsequent generation of a plant or animal requires the time effective and reliable generation of nucleic acid from potential parents. The present invention can be used for the isolation of either soluble or solid phase genetic material to provide effective and reliable results in such a need.

Likewise, the present invention, in the form of microplates, a tube or a chip, can be used for the generation and detection of genetic material. The present invention provides methodology for superior template preparation time (whether soluble or solid) and cost effective archiving.

Pressing a media, in the form of a swab or otherwise, enables the user to pick up any contaminated microbes on food products of any type. Genetic material isolated from the media can then be utilized for any manner of diagnostic procedure depending on whether soluble or solid phase genetic material is required. This analysis can be done almost effectively immediately, as opposed to prior art techniques.

By the use of genetic manipulation techniques, food stuff has been produced with increased size, flavor, ripening, and sugar content Many countries prohibit the sale of genetically modified food products and therefore require testing to be carried out. Since one is looking for specific genes that generate these characteristics, genetic material is required. The present invention can be used to provide rapid purification of both soluble and solid phase genetic material.

In view of the above, the present invention finds utility in various areas of genomics.

The present invention can further be utilized in the areas of purification from a patient's whole blood. Currently, genomic DNA is typically purified from a patient's whole blood, the genetic material present in the leukocyte population. Methods of genomic DNA extraction often involve many steps and involve several buffers and purification matrices. Recently, several new methodologies for genomic DNA extraction have been available.

One is the FTA 31 ET isolation exploited by Fitzco-Whatman. Another is the method described by Cambridge Molecular Technologies Ltd., UK (CMT), using Whatman F58301 (GF/L) material. The Fitzco-Whatman method utilizes an FTA coat on a 31 ET cellulosic material that spontaneously lyses leukocytes releasing the genomic DNA. This promotes integration and binding with the media. The DNA is fixed permanently to the media as no methodology for elution of DNA from the prior art FTA coated 31 ET was determined. For many applications, the fact that the genomic DNA bound to the 31 ET media cannot be eluted poses no problem whatsoever. PCR and RFLP are readily performed on the bound template. However, for genotyping experimental where many PCR reactions are carried on the same DNA population, the process of having to punch out different 1 millimeter disks for every primer set used is too time consuming to be efficient.

The present invention provides an ideal solution by allowing for elution of the DNA thereby providing a soluble DNA for each of the reactions performed.

Specifically, the CMT method utilizes Whatman GF/L glass fiber that has been shown to specifically capture leukocytes from whole blood application. Upon cellular capture, a lysis buffer is introduced and the released genomic DNA binds to the GF/L. The genomic DNA-GF/L binding is a strong enough interaction to withstand several washing steps. After washing, the GF/L bound genomic DNA is eluted with the application of water or TE buffer to the filter at preferably 82° C. As discussed above, a range of temperatures and buffers can be used. The GF/L media ensures leukocyte capture from whole blood. The coating of the present invention promotes lysis of the cells without the addition of inconvenient lysis buffers and steps. The genomic DNA stays bound to the GF/L media during washing steps. Full elution of the bound genomic DNA is achieved with the addition of water or buffer at the appropriate temperature, preferably 80° C.

With the genomic DNA in a soluble format, many PCR reactions can be carried out from the same DNA population with simple alaquating of the template rather than cumbersome punching. Likewise, an FTA coated GF/L matrix can be incorporated into a single tube, as discussed above, of a microplate device depending on the degree of throughput required.

The above examples show the various utilities of the present invention and are not meant to be limiting.

EXAMPLES

Example 1

Heat Elution:

Several drops of freshly finger-stick drawn blood was spotted to the filter membrane of the invention and allowed to air-dry for two minutes. Once dried two 1 mm diameter punches were taken from the dried blood spot and applied to individual 200 ul polypropylene PCR tubes. To each tube containing a single 1 mm blood punch, 200 ul of FTA Purification Reagent (Fitzco, Inc) was added. Per 500 ml: 0.29 g NaCl; 5 ml 1 M Tris pH 7.5; 1 ml 0.5 M EDTA; 2.5 ml TRITON-X-100 (t-Dctylphenoxypolyethoxyethanol), a non-ionic surfactant. Tubes were incubated for five minutes at room temperature with no shaking. Following incubation the FTA purification Reagent was aspirated from the tube. A second aliquot of 200 ul of FTA Purification Reagent was added to each tube. The tubes were incubated for five minutes at room temperature without shaking. Following incubation the FTA Purification Reagent was aspirated from both tubes. 200 ul of TE (10 mM Tris-HCl, 1 mM EDTA, pH 8.0) buffer was then added to each tube. The tubes were incubated for five minutes at room temperature without shaking. The TE buffer was then fully aspirated from both tubes, leaving the now washed 1 mm disc at the bottom of each tube. 20 ul of nuclease free water was then applied to both tubes. One tube was incubated at 82° C. for 10 minutes; the other was incubated at 95° C. for 10 minutes in a Biometra thermacycler. Following heat incubations the 20 ul of nuclease free water was aspirated from each tube and retained. An Amelogenin PCR amplification master mix was made up according to manufacturer's instructions (Promega), with a 25 ul aliquot applied to both tubes containing the 1 mm punches, and a 5 ul aliquot applied to both 20 ul nuclease free water samples. PCR was carried out following parameters described by the manufacturer of the Amelogenin primer set (Promega). Following PCR 10 ul of each PCR reaction was visualized on a 1.5% agarose gel stained with ethidium bromide.

Figure 1:
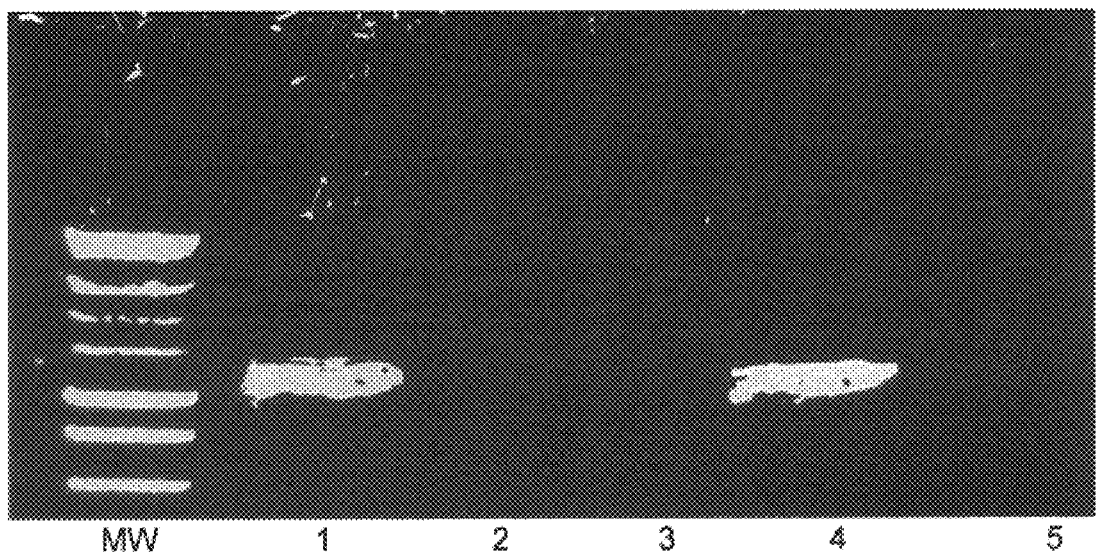
FIG. 1 is a digital representation of a gel showing the effect of differ ent heat elution regimes on blood genomic DNA bo und to the filter membrane of the invention with respect to Amelogenin PCR amplification; PCR products being noted at 218bp, lane 1: blood spotted 1 mm filter disk with 82° C., 10 minute incubation, lane 2: 82° C. eluted fraction, lane 3: blood spotted 1 mm filter disk with 95° C., 10 minute incubation, lane 4: 95° C. eluted fraction, lane 5: no DNA control.

It can be seen from the Amelogenin amplification results (FIG. 1), that nucleic acid immobilized to the filter membrane of the invention is not readily removed from the solid support following 82° C. heat incubation. Amplification product is noted from the 1 mm solid punch, but is not present in the 20 ul nuclease free water fraction. At 95° C. heat incubation we see that nucleic acid is eluted from the filter membrane of the invention. Amplification product is not detected from the 1 mm solid punch, but is present in the nuclease free water fraction.

Example 2

Full Elution Protocol:

Several drops of freshly finger-stick drawn blood were spotted to the filter membrane of the invention and allowed to air-dry for two minutes. Once dried two 1 mm diameter punches were taken from the dried blood spot and applied to individual 200 ul polypropylene PCR tubes. To each tube containing a single 1 mm blood punch, 200 ul of FTA Purification Reagent (Fitzco, Inc) was added. Tubes were incubated for five minutes at room temperature with no shaking. Following incubation the FTA purification Reagent was aspirated from the tube, 20 ul of the aspirate was retained. A second aliquot of 200 ul of FTA Purification Reagent was added to each tube. The tubes were incubated for five minutes at room temperature without shaking. Following incubation the FTA Purification Reagent was aspirated from both tubes, 20 ul of the aspirate was retained. 200 ul of TE buffer was then added to each tube. The tubes were incubated for five minutes at room temperature without shaking. The TE buffer was then fully aspirated from both tubes, leaving the now washed 1 mm disc at the bottom of each tube.

To one of the tubes, 20 ul of nuclease free water was then applied, and then incubated at 95° C. for 10 minutes in a Biometra thermacycler. Nothing was added to the other tube containing a 1 mm punch. Following heat the incubation of one of the tubes; the 20 ul of nuclease free water was aspirated and retained. An Amelogenin PCR amplification master mix was made up according to manufacturer's instructions (Promega), with a 25 ul aliquot applied to the tube containing the 1 mm punch that had not been subjected to heat incubation, and also the 1 mm punch that had been subjected to heat incubation. A 5 ul aliquot of master mix was applied to the 20 ul nuclease free water samples of the heat incubation punch, as well as the 20 ul aliquots taken from both FTA Purification Reagent incubations. PCR was carried out following parameters described by the manufacturer of the Amelogenin primer set (Promega). Following PCR 10 ul of each PCR reaction was visualized on a 1.5% agarose gel stained with ethidium bromide.

Figure 2:
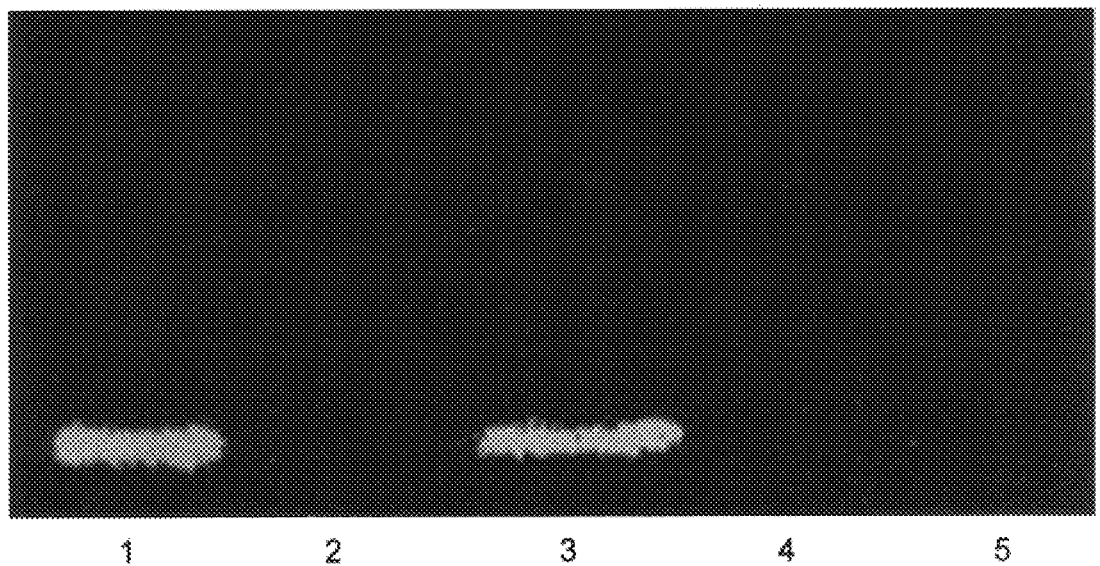
FIG. 2 is a digital representation of a gel showing the results of a full elution protocol for blood genomic DNA bound to the filter membrane of the invention with respect to Amelogenein PCR amplification, PCR products being noted at 218bp, lane 1: blood spotted 1 mm filter disk processed with no elution step, lane 2: blood spotted 1mm filter disk processed with an elution step, lane 3: eluted fraction, lane 4: wash step 1, lane 5: wash step 2.

It can be seen from the Amelogenin amplification results (FIG. 2) that nucleic acid from a whole cell source is immobilized to the filter membrane of the invention and does not elute from the solid support during washing steps. This is illustrated with amplification product detected from the 1 mm punch processed with no heat elution step, and the lack of amplification product detected in both FTA Purification Reagent washing steps. Complete elution, or release, of the immobilized nucleic acid following heat incubation is illustrated by amplification product detected in the 20 ul nuclease free water aspirate, and none detected from the 1 mm punch subjected to heat incubation. Example 2 indicates that all of the nucleic acid that has been initially immobilized to the filter membrane of the invention remains bound during washing steps, and is fully recovered into a soluble fraction following 95° C. heat incubation.

Example 3

Figures 3A, 3B:
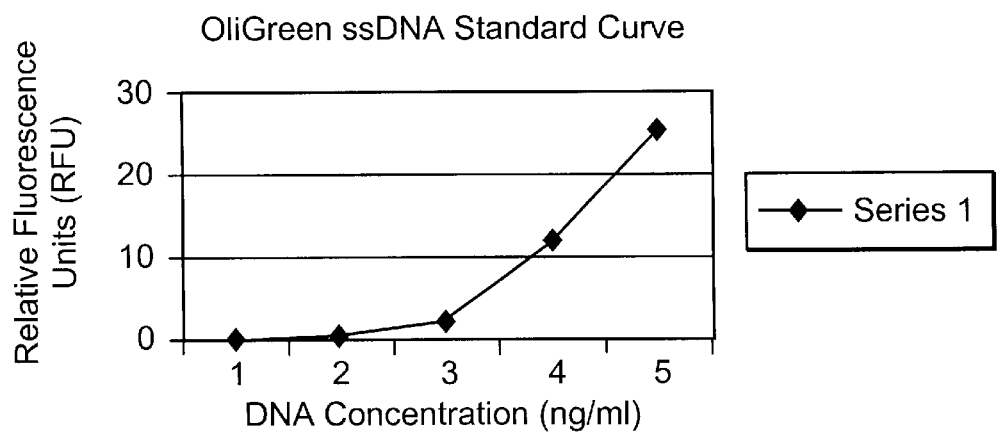
FIG. 3a shows OliGreen Fluorescent probe ss genomic DNA standard curve.
FIG. 3b shows Relative Fluorescent Units (RFU) and calculated yields of eluted ss genomic DNA from blood spotted to the filter material of the invention and cellulosic FTA filter card.

Comparison of Elution:

Single stranded DNA can be readily detected with the use of OliGreen$^R$ (Molecular Probes, Inc), a fluorescent probe specific for the single stranded molecule. By using OliGreen the total single stranded DNA eluted from the filter membrane of the invention can be determined, as well as other single stranded DNA purification methods. A standard curve for single stranded genomic DNA was constructed according to manufacturer's instructions (Molecular Probes, Inc) (see FIG. 3a).

5 ul of freshly finger-stick drawn blood was spotted to a 7 mm disk of the filter membrane, composed of a chemically coated porous glass microfiber filter membrane, of the invention and also to a 7 mm disk of the commercially available FTA solid support. Both spots were allowed to air-dry for two minutes. Once dried, the punches were applied to individual 1.5 ml polypropylene Eppendorf tubes. To each tube containing a single 7 mm blood punch, 1 ml of FTA Purification Reagent (Fitzco, Inc) was added.

Tubes were incubated for five minutes at room temperature with no shaking. Following incubation the FTA purification Reagent was aspirated from both tubes. A second 1 ml aliquot of FTA Purification Reagent was added to each tube. The tubes were incubated for five minutes at room temperature without shaking. Following incubation, the FTA Purification Reagent was aspirated from both tubes. 1 ml of TE buffer was then added to each tube. The tubes were incubated for five minutes at room temperature without shaking.

The TE buffer was then fully aspirated from both tubes, leaving the now washed 7 mm punches at the bottom of each tube. To both tubes, 200 ul of nuclease free water was applied, and then incubated at 100° C. for ten minutes in a water bath.

Following heat incubation, the nuclease free water fraction were aspirated from both tubes and immediately chilled on ice. 50 ul of the nuclease free water fraction of both samples was then subjected to OliGreen fluorometric quantitation according to the manufacturer's instructions (Molecular Probes, Inc). Relative fluorescent units (RFU) were taken for each sample, and with use of the standard curve (FIG. 3a) the total yields of the eluted DNA calculated (dilution factor for quantitation is 4-fold, total volume of eluate is 200 ul).

Typically from 5 ul of whole blood one can expect between 35,000 and 50,000 white blood cells; each cell containing approximately 7 pg of genomic DNA (A. Eisenberg, personal communication). Taking the upper limit, 350 ng of total genomic DNA is expected from 5 ul of whole blood. From the OliGreen quatitation data (FIG. 3b) it can be seen that 300 ng of total genomic DNA is recovered from the filter membrane of the invention, representing almost 100% of the expected yield. 60.2 ng of total genomic DNA is recovered from 5 ul of whole blood spotted to FTA solid support. Example 3 illustrates that the filter membrane of the invention exhibits a nucleic acid elution characteristic that is not apparent for the FTA solid support. Also from 5 ul of whole blood, approaching 100% of the available genomic DNA present within the sample cells can be isolated as a soluble fraction.

Example 4
Genomic DNA oreparation from Saliva:

Genomic DNA can be readily purified from many different cell sources. One of the most common sources, particularly in forensics and for its non-invasive collection, is saliva containing buccal epithelial cells. Although easy to collect, saliva does exhibit some difficulty for genomic DNA purification in that it is extremely viscous and not easily applied to column chromatography. Also PCR inhibitors are present within the mucus of saliva.

5, 10, 50, and 100 ul of female saliva were applied to individual 7 mm punches of the filter membrane of the invention. The saliva-spotted 7 mm punches were air dried for two minutes. Once dried, the punches were applied to individual 1.5 ml polypropylene Eppendorf tubes. To each tube containing a single 7 mm saliva punch, 1 ml of FTA Purification Reagent (Fitzco, Inc) was added. Tubes were incubated for five minutes at room temperature with no shaking. Following incubation, the FTA purification Reagent was aspirated from both tubes. A second 1 ml aliquot of FTA Purification Reagent was added to each tube.

The tubes were incubated for five minutes at room temperature without shaking. Following incubation the FTA Purification Reagent was aspirated from both tubes. 1 ml of TE buffer was then added to each tube. The tubes were incubated for five minutes at room temperature without shaking. The TE buffer was then fully aspirated from both tubes, leaving the now washed 7 mm punches at the bottom of each tube. To both tubes, 200 ul of nuclease free water was applied, and then incubated at 100° C. for ten minutes in a water bath. Following heat incubation, the nuclease free water fraction were aspirated from all tubes and immediately chilled on ice. 50 ul of the nuclease free water fraction of all samples was then subjected to OliGreen fluorometric quantitation according to the manufacturer's instructions (Molecular Probes, Inc). Relative fluorescent units (RFU) were taken for each sample, and with use of the standard curve (3a) the total yields of the eluted DNA calculated (dilution factor for quantitation is 4 fold, total volume of eluate is 200 ul). 10 ul of the nuclease free water fraction of six female saliva samples (5 ul) spotted to the filter membrane of the invention and subjected to same processing steps as above, was utilized as the template for 25 ul reaction volume Amelogenin PCR amplification according to manufacturer's instructions (Promega).

It can be seen (FIG. 4a) that genomic DNA can be isolated as a soluble fraction from saliva spotted to the filter membrane of the invention. The relationship between saliva starting volume and total DNA yield is given. The increase in yield of soluble genomic DNA does not show a linear relationship with respect to starting saliva volume, this is probably due to the filter membrane of the invention becoming saturated with saliva volume, with the capacity reaching a maximum at around 50 ul.

Figures 4A, 4B:
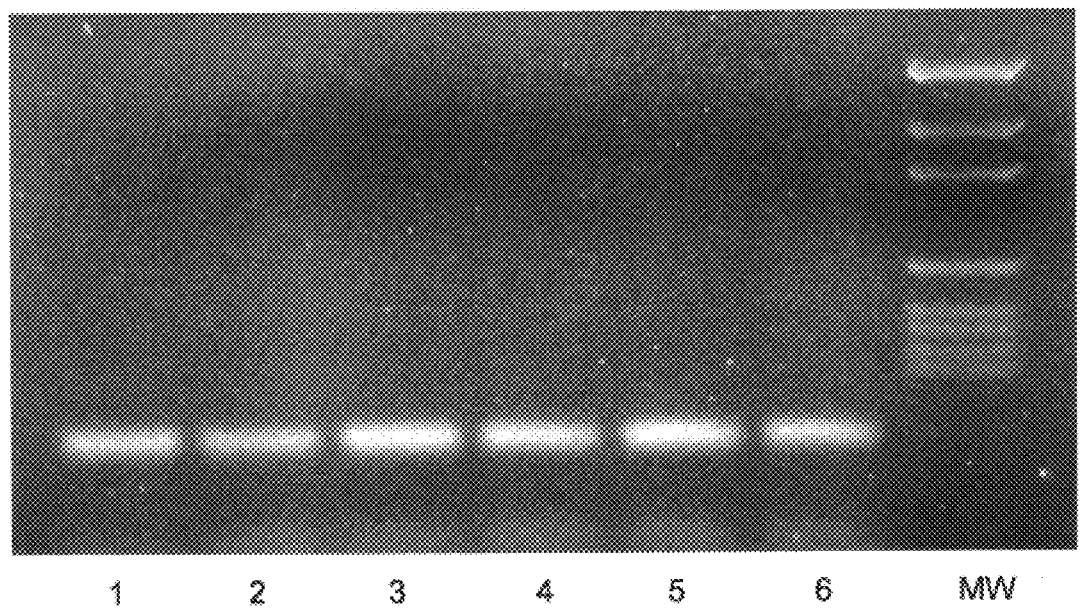
FIG. 4a shows average calculated total yields of eluted genomic DNA from different quantities of saliva applied to the filter membrane of the invention.
FIG. 4b shows a digital representation of an Amelogenein PCR amplification of six individual genomic DNA purifications from female saliva using the filter membrane of the invention, a PCR product of 218 bp being expected, lane MW: pGEM molecular weight markers, lanes 1–6: individual female saliva genomic DNA samples.

Amelogenin PCR amplification can be demonstrated for all of nuclease free water elution fractions from 5 ul of starting saliva spotted to the filter membrane of the invention (FIG. 4b).

Example 5
Downstream Use of Eluted DNA:

Tissue typing is a generic genotyping technique that is a common practice within the clinical community. Often blood is taken from a potential donor and their tissue type determined by a combination of allelespecific PCR followed by hybridization.

5 ul of freshly acquired male whole blood was applied to six 7 mm punches of the filter membrane of the invention. The punches were then applied to a 1.5 ml polypropylene Eppendorf tubes. To the tubes containing a single 7 mm blood punch, 1 ml of FTA Purification Reagent (Fitzco, Inc) was added. The tubes were incubated for five minutes at room temperature with no shaking. Following incubation, the FTA purification Reagent was aspirated from the tubes. A second 1 ml aliquot of FTA Purification Reagent was added to the tubes. The tubes were incubated for five minutes at room temperature without shaking. Following incubation the FTA Purification Reagent was aspirated from the tubes. 1 ml of TE buffer was then added. The tubes were then incubated for five minutes at room temperature without shaking. The TE buffer was then fully aspirated from the tubes, leaving the now washed 7 mm punches at the bottom. 200 ul of nuclease free water was applied, and the tubes then incubated at 100° C. for 10 minutes in a water bath. Following heat incubation the nuclease free water fraction was aspirated from the tubes and 10 ul of each used for either HLA-A PCR amplification or HLA-B PCR amplification. Both PCR amplifications were carried out according to manufacturer's directions (Lifecodes, Inc). 10 ul of each amplification reaction was visualized on a 1.5% agarose gel with ethidium bromide staining.

Figure 5A:
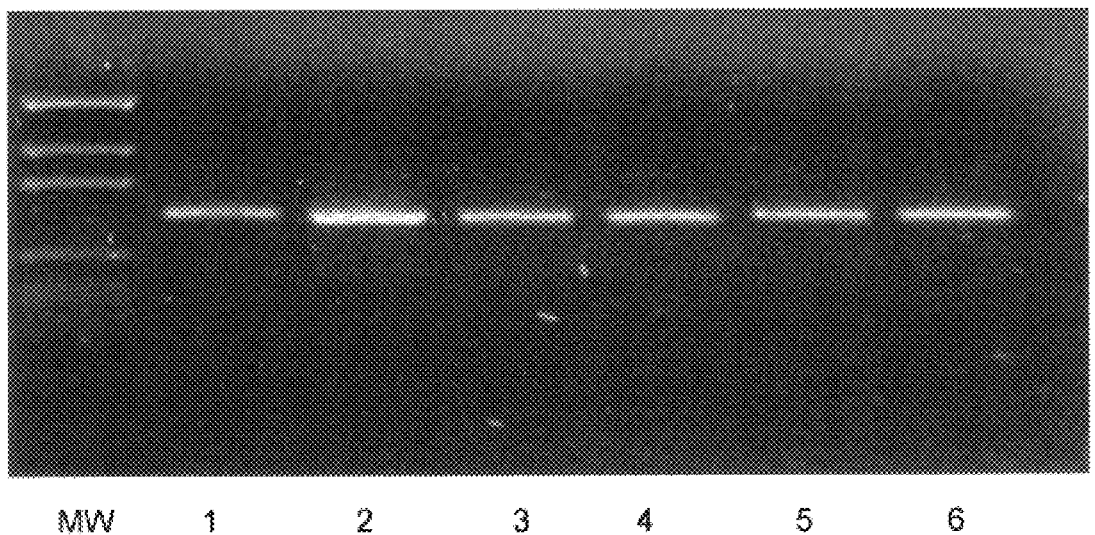
FIG. 5a is a digital representation of a gel showing tissue typing using HLA-A primers on individual male blood samples. A PCR product of 900 bp is expected to be amplified, lane MW: pGEM molecular weight markers, lanes 1–6: individual male blood genomic DNA samples.
Figure 5B:
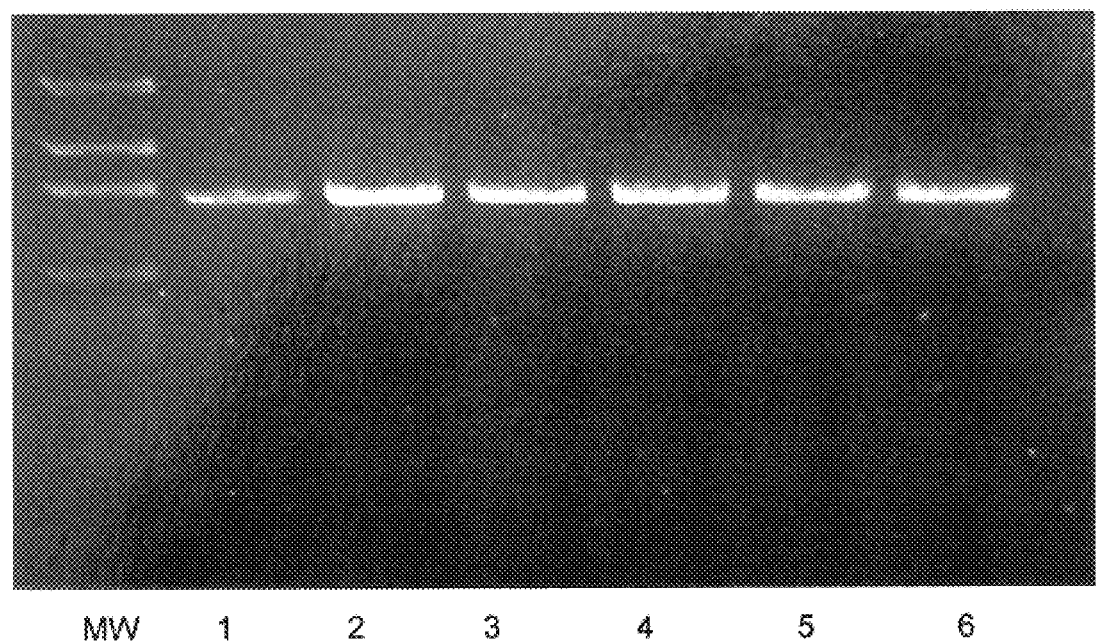
FIG. 5b shows a digital representation of a gel of tissue typing using HLA-B primers on individual male blood samples, a PCR product of 1090 bp is expected to be amplified, lane MW: pGEM molecular weight markers, lane 1–6: individual male blood genomic DNA samples.

All of the nuclease free water fractions acquired from the blood samples spotted to the filter membrane of the invention give PCR amplification product for HLA-A (FIG. 5a), and HLA-B (FIG. 5b). Example 5 illustrates the validity of soluble genomic DNA purification from blood using the filter membrane of the invention, providing a soluble DNA fraction that can be utilized for typical genotyping amplification reactions. The generation of a 1 kb amplification product illustrates the high quality of the isolated soluble genomic DNA fraction.

FIG. 6. Filter Membrane of the Invention Formats:

A main advantage of the filter membrane of the invention is that it is manufactured in the form of a filter paper reel.

Filter paper manufactured in this way is capable of being formatted to a variety of devices. Other genomic DNA purification media such as polymeric resin for example cannot be formatted in the same way. For example it is suitable for a filter material to be designed in a swab configuration—it would be extremely difficult to propose the same format for chromatographic resin. The desired format for the filter membrane of the invention is dependent upon the application.

Saliva represents a very difficult sample in that it is a viscous fluid. Traditional column chromatography, or spin tubes are not devices for handling it. To that end, the filter membrane of the invention was formatted in the configuration of a 7.5 mm free-floating disk held within a 2 ml Eppendorf tube. With such a device, saliva can be directly administered from the donor's mouth. Because the filter membrane of the invention is free floating within the tube, there will be no change of filter clogging which results in poor recovery.

Six saliva samples of approximately 100 ul each were directly administered to individual tubes containing a free-floating disk of the filter membrane of the invention. To each tube containing a single 7.5 mm saliva disk, 1 ml of FTA Purification Reagent (Fitzco, Inc) was added. Tubes were incubated for five minutes at room temperature with no shaking. Following incubation the FTA purification Reagent was aspirated from the tubes. A second 1 ml aliquot of FTA Purification Reagent was added to each tube. The tubes were incubated for five minutes at room temperature without shaking.

Following incubation, the FTA Purification Reagent was aspirated from the tubes. 1 ml of TE buffer was then added to each tube. The tubes were incubated for five minutes at room temperature without shaking. The TE buffer was then fully aspirated from the tubes, leaving the now washed 7.5 mm disks at the bottom of each tube.

Figure 6A:
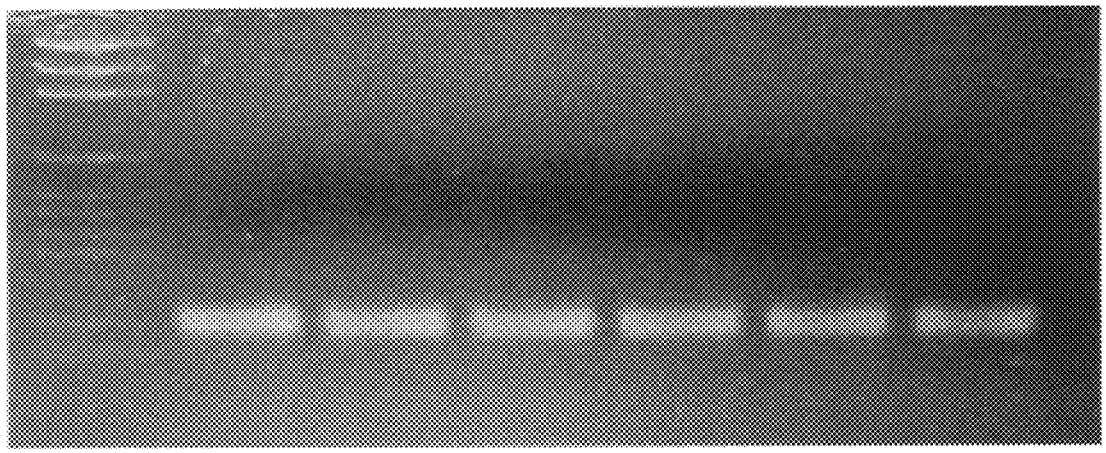
FIG. 6a is a digital representation of a gel showing results from Amelogenin PCR amplification of DNA purified from 6 individual saliva samples using the filter membrane of the invention in the format of a 7 mm free-floating disc in a microtube, lane MW: pGEM molecular weight markers, lanes 1–6: individual saliva genomic DNA.

To all tubes, 200 ul of nuclease free water was applied, and then incubated at 100° C. for 10 minutes in a water bath. Following heat incubation the nuclease free water fractions were aspirated from all the tubes and 10 ul of each eluate applied to 25 ul Amelogenin PCR amplification reactions according to manufacturer's instructions (Promega). 10 ul of each reaction was visualized on a 1.5% agarose gel and ethidium bromide staining (FIG. 6a). The free-floating disk for the filter membrane of the invention can be utilized for recalcitrant samples such as saliva.

Figure 6B:
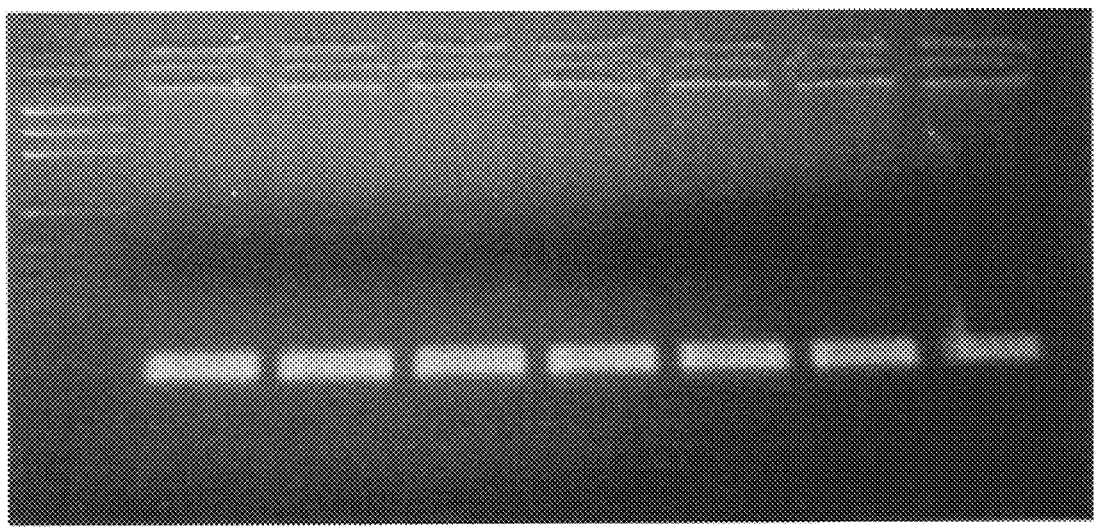
FIG. 6b shows Amelogenin PCR amplification of DNA purified from 7 individual blood samples using the filter membrane of the invention in the format of a microcentrifuge spin basket, lane MW: pGEM molecular weight markers, lanes 1–7: individual blood genomic DNA.

The filter membrane of the invention can be formatted to a spin microfuge device. Such a device has been shown to be an extremely quick tool for the isolation of nucleic acids (see Qiagen catalog). Three layers of 7.4 mm disks of the filter membrane of the invention were configured into the spin basket of seven spin microfuge devices. 5 ul of seven individual male blood samples were applied to the filter disk of each spin basket. 0.5 ml of FTA Purification Reagent (Fitzco Inc) was added to the basket. The microfuge tubes containing the basket was then centrifuged at 6000 xg for one minute. The resultant filtrates were discarded from the microfuge tubes. 0.5 ml of FTA Purification Reagent was again added to the filter baskets and again the tubes centrifuged at 6000 xg for one minute. Following the removal of the filtrates from the microfuge tubes, 0.5 ml of TE buffer was added to the baskets. This was followed by the same centrifugation regime described above. After the TE buffer centrifugation step, 200 ul of nuclease free water was added to the baskets of the microfuge tubes. The microfuge tubes was then incubated at 100° C. for fifteen minutes in a water bath. Following heat incubation the microfuge tubes were centrifuged at 12,000 xg for two minutes to recover the nuclease free water fractions. 10 ul of each nuclease free water fraction was applied to 25 ul Amelogenin PCR amplification reactions according to manufacturer's instructions (Promega). 10 ul of each reaction was visualized on a 1.5% agarose gel and ethidium bromide staining (FIG. 6b).

The spin microfuge device that contains the filter membrane of the invention can be utilized to isolate soluble genomic DNA from whole blood in less than 20 minutes. The quality of the genomic DNA isolated is demonstrated with 100% PCR amplification of the samples evaluated.

Buccal scrapes are often used as a means for the collection of nucleic acid containing samples such as epithelial cells, particularly in population field studies such as offender identification. The filter membrane of the invention can be formatted in the configuration of a swab that can be directly administered into the mouth of the donor. By scraping the swab along the inside of the donor's cheek, epithelial cells can be collected on the filter membrane of the invention. Other genomic DNA purification tools such as chromatographic resin cannot be readily configured to swabs that are applied to donors' mouths.

Figure 6C:
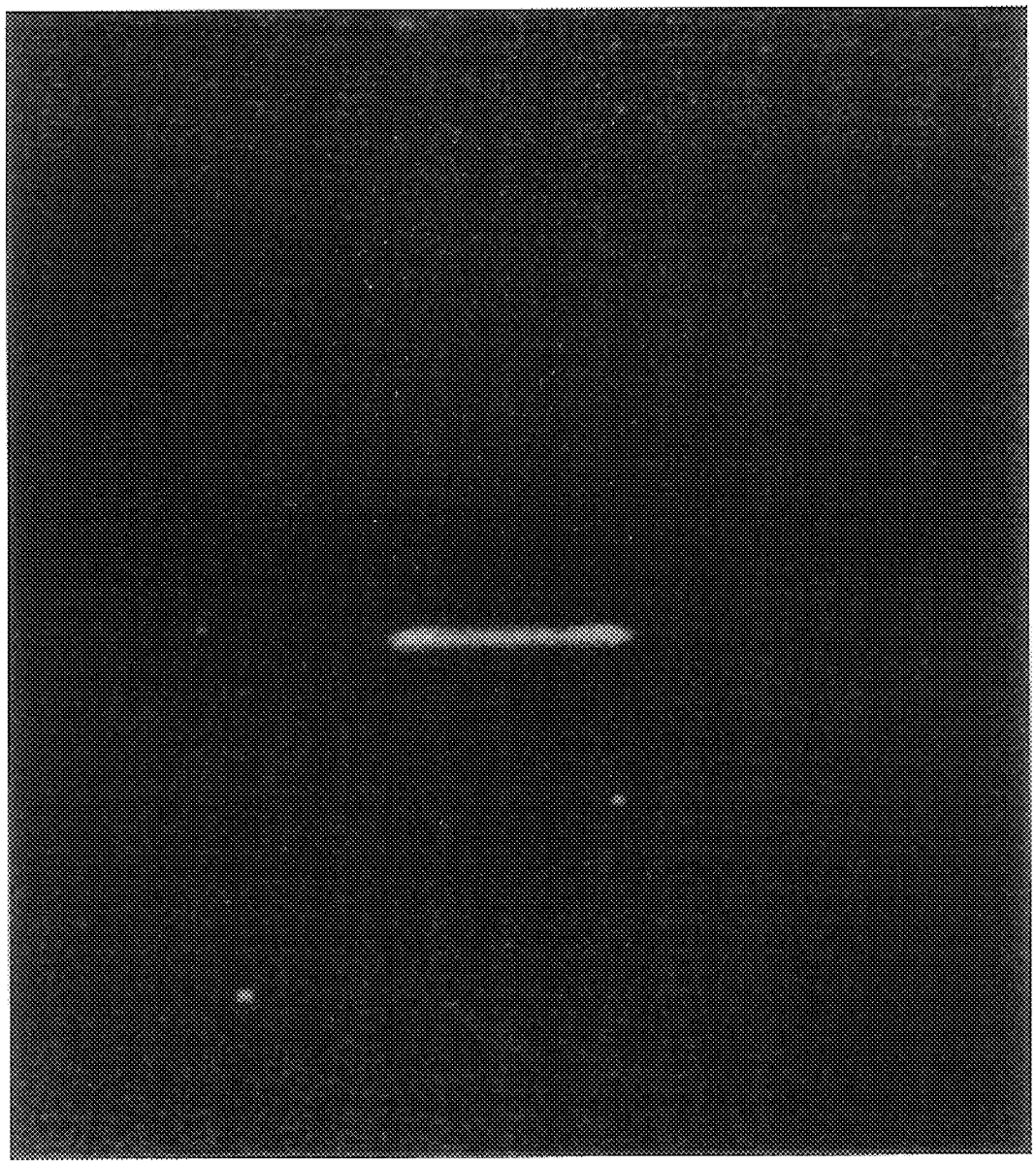
FIG. 6c shows Amelogenin PCR amplification of DNA purified from a buccal scrape sample using the filter membrane of the invention in the format of a swab, lane 1: swab after elution step, lane 2: eluted fraction, lane 3: no DNA PCR control.

A small piece of the filter membrane of the invention was configured into the stem of a commercially available oral swab (Fitzco Inc). The swab was placed into the mouth of a male donor and scraped along the inside of the cheek for ten seconds. Following scraping, the filter membrane of the invention that constitutes the swab head was placed into a 1.5 ml Eppendorf tube. To the tube containing the swab head, 1 ml of FrA Purification Reagent (Fitzco, Inc) was added. The tube was incubated for five minutes at room temperature with no shaking. Following incubation, the FTA purification Reagent was aspirated from the tube. A second 1 ml aliquot of FTA Purification Reagent was added to each tube. The tube was incubated for five minutes at room temperature without shaking. Following incubation, the FTA Purification Reagent was aspirated from the tube. 1 ml of TE buffer was then added to the tube. The tube was incubated for five minutes at room temperature without shaking. The TE buffer was then fully aspirated from the tube, leaving the now washed swab head at the bottom of each tube. To all tubes, 200 ul of nuclease free water was applied, and then incubated at 100° C. for ten minutes in a water bath. Following heat incubation the nuclease free water fraction was aspirated from the tube and 10 ul of the eluate applied to 25 ul Amelogenin PCR amplification reaction according to manufacturer's instructions (Promega). A 1 mm punch was taken from the swab head following heat incubation and applied to a 25 ul Amelogenin PCR amplification according to manufacturer's instructions (Promega). 10 ul of each reaction was visualized on a 1.5% agarose gel and ethidium bromide staining (FIG. 6c). The filter membrane of the invention can be configured in the form of a swab that can be utilized to purify genomic DNA from buccal scrapes. The isolated soluble genomic DNA is of suitable quality for PCR amplification.

Example 7

Product Comparisons:

There are many genomic DNA purification systems that are commercially available. To illustrate the validity of the filter membrane of the invention, the device of the present invention was compared directly to the genomic DNA purification kits available from Roche Molecular Biochemicals (Split Second™) and Promega (AmpReady™).

5 ul of freshly drawn finger-stick blood was applied to both commercial kits and to the filter membrane of the invention. Procedure was followed according to manufacturers directions for both of the commercial kits. 5 ul of freshly finger-stick drawn blood was spotted to a 7 mm disk of the filter membrane of the invention. The punch was applied to a 1.5 ml polypropylene Eppendorf tube. To the tube containing a single 7 mm blood punch, 1 ml of FTA Purification Reagent (Fitzco, Inc) was added. The tube was incubated for five minutes at room temperature with no shaking. Following incubation the FTA purification Reagent was aspirated from the tube. A second 1 ml aliquot of FTA Purification Reagent was added to the tube. The tube was incubated for five minutes at room temperature without shaking.

Following incubation, the FTA Purification Reagent was aspirated from the tube. 1 ml of TE buffer was then added to the tube. The tubes were incubated for five minutes at room temperature without shaking. The TE buffer was then fully aspirated from the tube, leaving the now washed 7 mm punches at the bottom of the tube.

To the tube, 200 ul of nuclease free water was applied, and then incubated at 100° C. for ten minutes in a water bath. Following heat incubation the nuclease free water fraction was aspirated from both tubes and immediately chilled on ice. 50 ul of the nuclease free water fraction was then subjected to OliGreen fluorometric quantitation according to the manufacturer's instructions (Molecular Probes, Inc).

The same OliGreen quantitation was carried out for both the Roche Molecular Biochemical and Promega purified genomic DNA samples. Relative fluorescent units (RFU) were taken for all samples, and with use of the standard curve (3a) the total yields of the eluted DNA calculated (dilution factor for quantitation is 4-fold, total volume of eluate is 200 ul) (see FIG. 7b). A 10 ul aliquot of the genomic DNA produced from each protocol was applied to 25 ul Amelogenin PCR amplification reactions according to manufacturer's instructions (Promega). 10 ul of each reaction was visualized on a 1.5% agarose gel and ethidium bromide staining.

A table outlining the various steps for each protocol has been constructed (FIG. 7a) and illustrates that the filter membrane of the invention requires fewer hands on operations and can be completed in a similar, or faster, amount of time as the commercial kits.

Figure 7C:
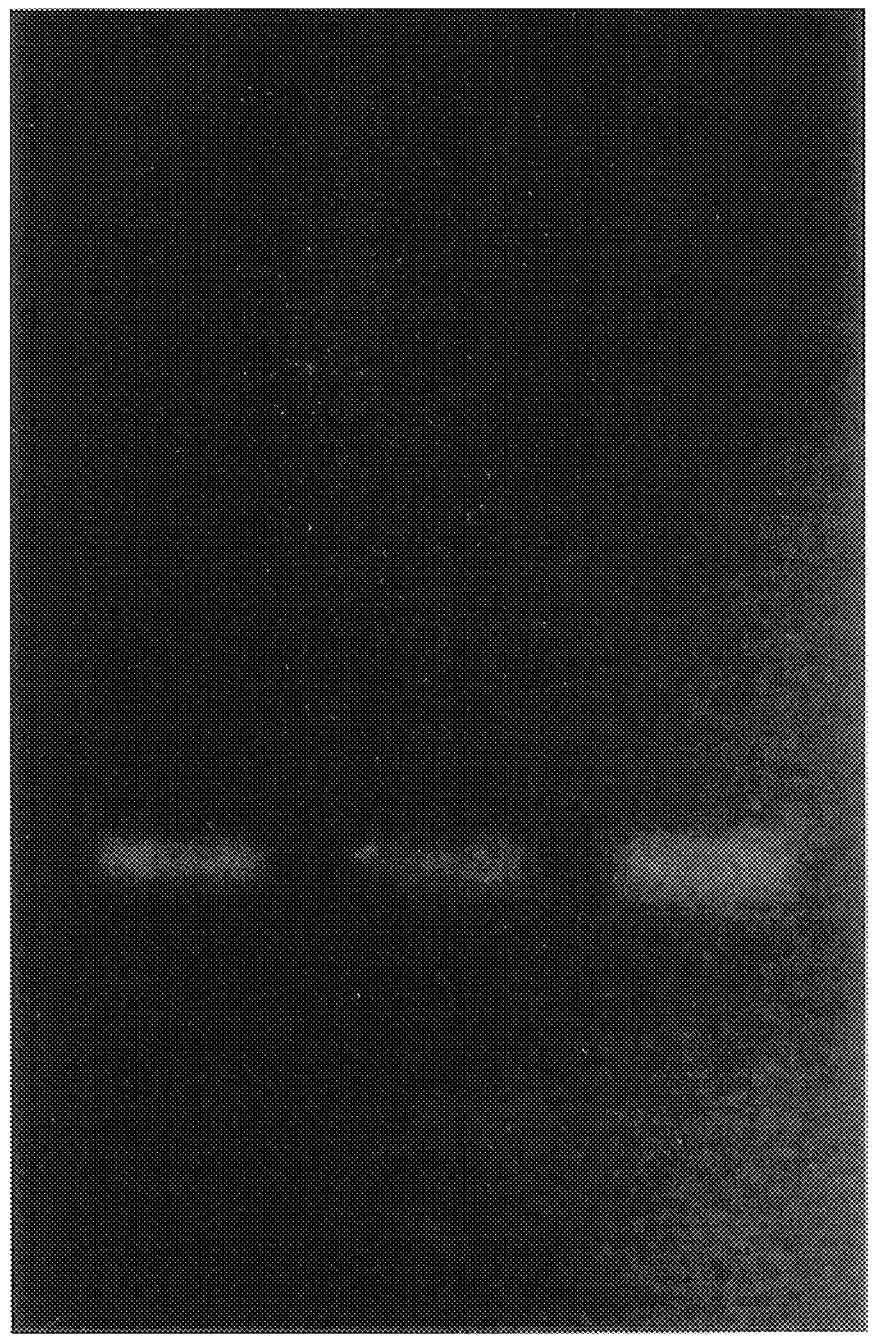
FIG. 7c is a digital representation of a gel showing Amelogenin PCR amplification of purified genomic DNA from blood using commercially available kits compared to the filter membrane of the invention, lane 1 filter membrane of the invention, lane 2: Roche kit, lane 3: Promega kit.

Amelogenin PCR amplification is successful for all methodologies evaluated (FIG. 7c). The filter membrane of the invention provides a method for genomic DNA isolation that is comparable to commercially available kits in terms of speed, yield, and PCR template quality.

Example 8

Archiving Blood Samples:

The ability to archive nucleic acid containing samples such as blood or bacterial plasmid clones is extremely important for procedures where downstream processes have failed, "look-back" regimes in transfusion medicine are required, or genotyping of a patient that is no longer alive is needed. It has been demonstrated in U.S. Pat. Nos. 5,496,562; 5,756,126; and 5,807,527 that blood samples applied to FTA solid support can be kept stable, without nucleic acid damage, at room temperature for extended lengths of time. The characteristic is due in part to the chemical composition of the solid matrix. The filter membrane of the invention composes of the exact chemical composition as the FTA solid support, but differs to FTA with respect to the base filter material. The following experiment demonstrates that the present invention maintains the archiving capability of the prior art filters while providing the unexpected improvements of the present invention.

Several drops of freshly finger-stick drawn blood was spotted to the filter membrane of the invention and allowed to air-dry for two minutes. Once dried two 1 mm diameter punches were immediately taken from the dried blood spot and applied to individual 200 ul polypropylene PCR tubes. The remainder of the blood spot was placed into an airtight polypropylene bag and stored at room temperature on a laboratory bench-top for 19 weeks.

After 19 weeks storage, one 1 mm punch was taken from the blood spot and applied to a 200 ul polypropylene PCR tube. To each tube containing a single 1 mm blood punch, 200 ul of FTA Purification Reagent (Fitzco, Inc) was added. Tubes were incubated for five minutes at room temperature with no shaking.

Following incubation, the FTA purification Reagent was aspirated from the tube. A second aliquot of 200 ul of FTA Purification Reagent was added to each tube. The tubes were incubated for five minutes at room temperature without shaking. Following incubation, the FTA Purification Reagent was aspirated from the tubes. 200 ul of TE buffer was then added to each tube. The tubes were incubated for five minutes at room temperature without shaking. The TE buffer was then fully aspirated from both tubes, leaving the now washed 1 mm disc at the bottom of each tube. 20 ul of nuclease free water was then applied to both tubes. Tubes were then incubated at 95° C. for 10 minutes. Following heat incubations the 20 ul of nuclease free water was aspirated from each tube and retained.

An Amelogenin PCR amplification master mix was made up according to manufacturer's instructions (Promega), with a 25 ul aliquot applied to both tubes containing the 1 mm punches, and a 5 ul aliquot applied to 20 ul nuclease free water samples. PCR was carried out following parameters described by the manufacturer of the Amelogenin primer set (Promega). Following PCR 10 ul of each PCR reaction was visualized on a 1.5% agarose gel stained with ethidium bromide, and photographed using a Polaroid camera.

Figure 8A:
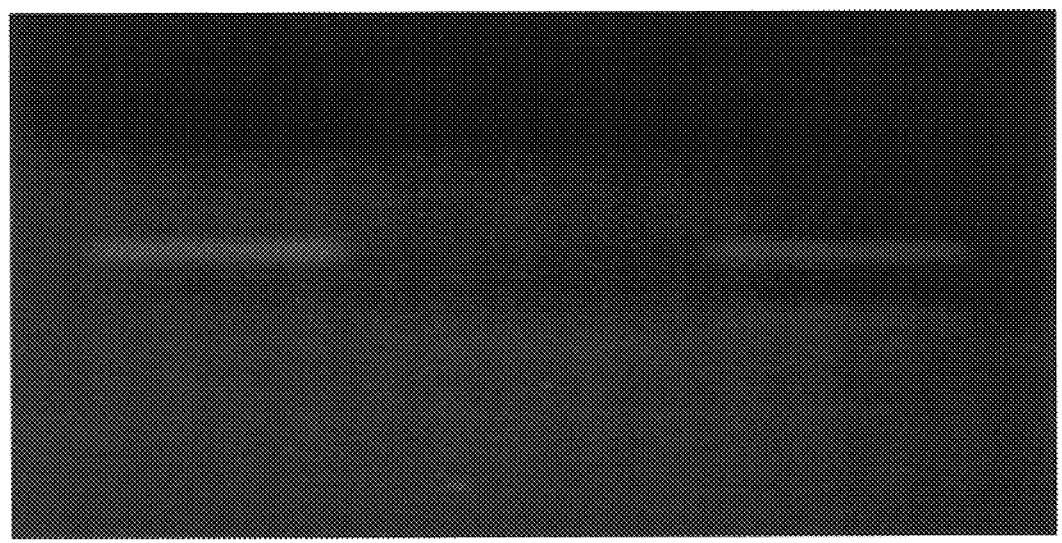
FIG. 8a is a digital representation of a gel showing Amelogenin PCR amplification of genomic DNA purified from day I spotted blood using the filter membrane of the invention, lane 1: blood spotted 1 mm filter disk processed with no elution step, lane 2: blood spotted 1 mm filter disk following an elution step, lane 3: eluted fraction.
Figure 8B:
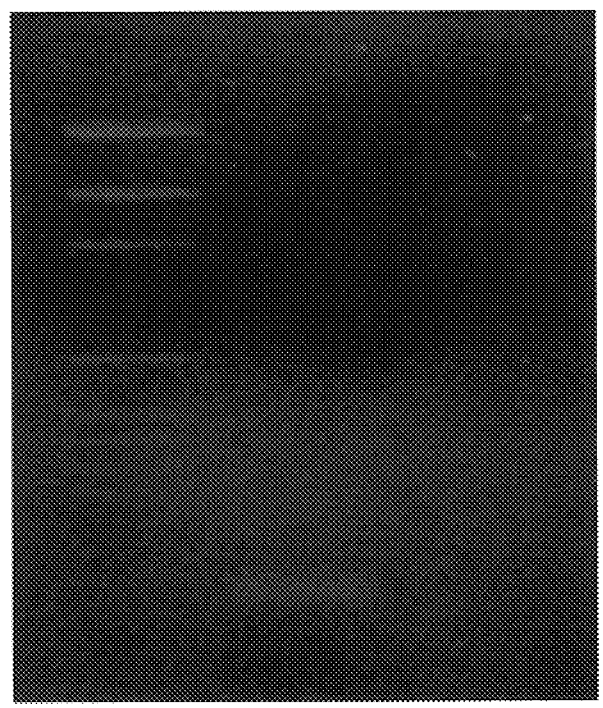
FIG. 8b shows Amelogenin PCR amplification of genomic DNA purified from 19 week old spotted blood using the filter membrane of the invention, lane MW: pGEM molecular weight markers, lane 1: eluted fraction, lane 2: blood spotted 1 mm filter disk following an elution step.

Example 8 illustrates that soluble genomic DNA isolation and PCR amplification can be carried out from fresh blood spotted to the filter membrane of the invention at day 1 (FIG. 8a). The same blood sample spotted to the filter membrane of the invention can also be processed to give soluble isolated genomic DNA that is suitable for PCR amplification (FIG. 8b). The filter membrane of the invention exhibits the same sample archive characteristics as the FTA solid support. Along with the demonstrated archive characteristic, the filter membrane of the invention differs from FTA solid support in that immobilized nucleic acid can be readily released from the solid filter matrix.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claim is:

1. A method of storing a genetic material and subsequently analyzing the genetic material by the steps of contacting cells having genetic material with a glass microfiber matrix sorbed with a FTA purification reagent while enabling cellular lysis and release of genetic material from the lysed cells, immobilizing and stabilizing the released genetic material, and disposing the matrix having the genetic material immobilized therein into heated water in the temperature range of 65° C. to 100° C. and releasing the genetic material into the heated water to generate a soluble genetic material fraction; and analyzing the eluted genetic material.

2. A method as in claim 1, wherein said eluting step is further defined as exposing the matrix to water, heating the water containing the matrix having the genetic sample immobilized thereon and releasing the heated genetic material from the heated matrix and into solution in the water.

3. A method as in claim 1 wherein the water is nuclease free.

4. A method as in claim 1 further including the step of washing the matrix having the genetic material immobilized therein prior to said eluting step.

5. A method as in claim 1 further including the steps of collecting a genetic material sample in a container containing the matrix; contacting the matrix with the genetic material and conducting said immobilizing and eluting steps within the container.

6. A method as in claim 1 further including the steps of spotting a blood sample on the matrix; drying the blood sample thereon; and subsequently immobilizing genetic material from the blood sample on the matrix.

7. A method as in claim 1 further including the steps of spotting a saliva sample on the matrix; drying the saliva sample on the matrix; and subsequently immobilizing genetic material from buccal epithelial cells contained in the saliva on the matrix.

8. A method as in claim 7 further including the steps of expectorating saliva into a container which contains the matrix to contact the matrix with the expectorated saliva and conducting said immobilizing and eluting steps within the same container.

9. A method as in claim 7 further defined as swabbing a buccual surface with the matrix to spot a buccal surface sample of saliva thereon.

10. A method as in claim 1 further defined as swabbing a surface with the matrix and then disposing the support in the container.

11. A method as in claim 1 wherein said analyzing step is further defined as amplifying the soluble genetic material and visualize the amplified genetic material.

12. A method as in claim 1 wherein said analyzing step is further defined as amplifying the soluble genetic material and labelling the amplified genetic material with a fluorescent probe.

13. A method as in claim 1 wherein said analyzing step is further defined as amplifying and fluorescently labelling genomic DNA in the soluble fraction.

14. A method as in claim 1 further including the steps of applying a genetic material sample to the matrix wherein the matrix is disposed within a spin basket of a spin microfuge device, spinning the basket, discarding a produced filter to perfect said immobilization steps and subsequently performing said eluting step.

15. A method of storing a genetic material by contacting cells having genetic material with a glass microfiber matrix sorbed with a FTA purification reagent that lyses cells, releases the genetic material from the lysed cells, and allows subsequent heat elution of the genetic material into heated water in a temperature range of 65° C. to 100° C. while stabilizing the immobilized released genetic material.

* * * * *